United States Patent [19]

Goldmann

[11] 4,349,675

[45] Sep. 14, 1982

[54] 4,4-DISUBSTITUTED SPIRO-1,4-DIHYDROPYRIDINES AND A PROCESS FOR THEIR PRODUCTION

[75] Inventor: Siegfried Goldmann, Wuppertal, Fed. Rep. of Germany

[73] Assignee: Bayer Aktiengesellschaft, Leverkusen, Fed. Rep. of Germany

[21] Appl. No.: 270,455

[22] Filed: Jun. 4, 1981

[30] Foreign Application Priority Data

Jun. 25, 1980 [DE] Fed. Rep. of Germany ....... 3023820

[51] Int. Cl.$^3$ ................... C07D 471/10; C07D 471/20
[52] U.S. Cl. ...................................... 546/17; 546/16; 544/330; 544/331
[58] Field of Search ................... 546/17, 16; 544/230, 544/231

[56] References Cited

PUBLICATIONS

Ong et al., "J. Med. Chem.", vol. 24, No. 1, (1981), pp. 74–79.

*Primary Examiner*—Robert T. Bond
*Attorney, Agent, or Firm*—Sprung, Horn, Kramer & Woods

[57] ABSTRACT

The invention relates to 4,4-disubstituted spiro-1,4-dihydropyridine compounds of formula (I). Also included in the invention are methods for producing the compounds of formula (I) by (a) cyclizing a compound of formula (II) in the presence of a base or (b) reducing a sulphinyl compound of formula (I) by means of Raney nickel.

The compounds of formula I are intermediates and can be converted to sulphur-free compounds of formula (III) which are known to be useful for treating circulatory illnesses.

12 Claims, No Drawings

4,4-DISUBSTITUTED SPIRO-1,4-DIHYDROPYRIDINES AND A PROCESS FOR THEIR PRODUCTION

The present invention relates to certain new, 4,4-disubstituted spiro-1,4-dihydropyridine compounds and to a new and unobvious process for their production. The compounds can be used as intermediate products for the synthesis of pharmaceuticals.

1,4-Dihydropyridines which are monosubstituted in the 4-position are readily accessible by the "Hantzsch synthesis" and are already known (see A Hantzsch Justus Lieb. Ann. Chem. 215, 1 (1882) and DT-OS (German Published Specification) 2,117,571).

1,4-Dihydropyridine-3,5-dicarboxylic acid ester derivates which carry two substituents in the 4-position could not hitherto be prepared by known methods (see B. Loev and K. M. Snader, J. Org. Chem. 30, 1914 (1965)). It is also only possible to carry out the addition of organometallic compounds onto pyridine derivatives if the 4-position of the pyridine is not already substituted (see R. Lukes and J. Kuthan, Collect. Czech. Chem. Comm. 26, 1845 (1961); J. Palacek, K. Vondra and J. Kuthan, ibid. 34, 2991 (1969) and J. F. Biellmann, H. J. Callot and M. P. Goeldner, Tetrahedron 26, 4655 (1970)).

According to the present invention there are provided compounds which are 4,4-disubstituted spiro-1,4-dihydro-pyridines of the formula

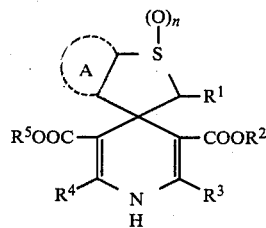

in which $A$ represents a carboxylic aryl radical (preferably a mono- or bi-cyclic carbocyclic aryl radical) or a heterocyclic radical selected from furyl, pyrryl, pyrazolyl, imidazolyl, oxazolyl, isoxazolyl, pyridyl, pyridazinyl, pyrimidyl, pyrazinyl, quinolyl, isoquinolyl, indolyl, benzimidazolyl, quinazolyl and quinoxalyl, the said carbocyclic aryl radical or heterocyclic radical optionally containing 1, 2 or 3 identical or different substituents selected from phenyl, alkyl, alkenyl, alkinyl, alkoxy, alkylene, dioxyalkylene, halogen, trifluoromethyl, trifluoromethoxy, alkylamino, dialkylamino, nitro, cyano, azido and carboxamido, $R^3$ and $R^4$ are identical or different and each represent a hydrogen atom or an achiral straight-chain or branched alkyl radical, an aryl radical or an aralkyl radical, $R^2$ and $R^5$ are identical or different and each represent a straight-chain, branched or cyclic, saturated or unsaturated hydrocarbon radical, which is optionally interrupted in the chain by hydrogen and is optionally substituted by halogen, pyridyl, phenyl or phenoxy, the phenyl or phenoxy group optionally being substituted by halogen, cyano, dialkylamino, alkoxy, alkyl, trifluoromethyl or nitro, $R^1$ represents a straight-chain, branched or cyclic, saturated or unsaturated aliphatic hydrocarbon radical which is optionally interrupted in the chain by one oxygen and is optionally substituted by phenyl, phenoxy and pyridyl or amino, the phenyl, phenoxy or pyridine radicals optionally being substituted by halogen, cyano, dialkylamino, alkoxy, alkyl, trifluoromethyl or nitro, and the amino group optionally being substituted by two identical or different substituents selected from alkyl, alkoxy-alkyl, aryl and aralkyl, and n is 0, 1 or 2.

As used herein and unless otherwise specified, the term "aryl" defines preferably mono- or bi-cyclic carbocyclic aryl and the term "aralkyl" defines preferably mono- or bi-cyclic carbocyclic aryl -$C_1$-$C_4$-alkyl. Also, the terms "alkyl", "alkenyl", "alkinyl" and "alkoxy" preferably contain up to 8, particularly up to 4 carbon atoms, the term "alkylene" preferably contains up to 6 carbon atoms; the term "dioxy-alkylene" preferably contains 4 carbon atoms; the term "halogen" preferably includes chlorine, fluorine and bromine; the terms "alkylamino" and "dialkylamino" preferably contain up to 4 carbon atoms in each alkyl group.

According to the present invention there is provided a process for the production of a compound of the present invention, in which (a) a pyridine of the general formula

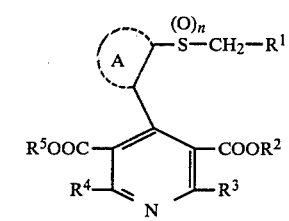

in which $R^1$, $R^2$, $R^3$, $R^4$, $R^5$, n and $A$ have the above-mentioned meanings, is cyclised at a temperature between $-120°$ C. and $+30°$ C. in the presence of a base and optionally in the presence of an inert organic solvent, to give a spiro compound of the general formula (I), and (b) if a compound of general formula (I) in which n is 0 is required and the product of reaction variant (a) is a sulphinyl compound (n is 1), that sulphinyl compound of formula (I) is reduced by means of Raney nickel.

If 2,6-dimethyl-4-(2-methylsulphinyl-phenyl)pyridine-3,5-dicarboxylic acid dimethyl ester is used as the starting substance, the course of the reaction variant (a) for the production of compounds according to the present invention is illustrated by the following equation:

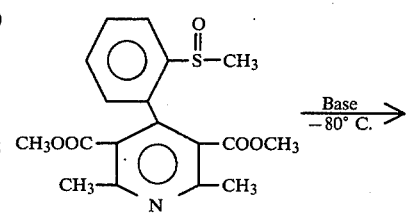

-continued

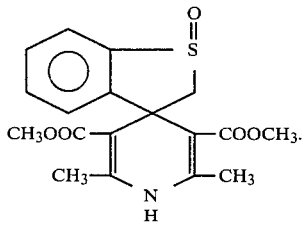

The pyridine compounds of the general formula (II) used as starting substances are novel, but they can be prepared from the corresponding 1,4-dihydropyridines by known oxidation processes, such as, for example, oxidation with chloranil (see J. Am. Chem. Soc. 79, 3477 (1957)). The 1,4-dihydropyridines are likewise prepared by known methods (see DT-OS (German Published Specification) No. 2,117,571 and U.S. Pat. No. 3,799,934; and J. Med. Chem. 17, 956 (1974)).

Preferred inert organic solvents which may be mentioned are ethers (such as diethyl ether, tetrahydrofuran or dioxane), and hydrocarbons, (such as benzine, petroleum ether, toluene or xylene).

As preferred bases which can be used according to the invention there may be mentioned metal hydrides (such as sodium hydride or potassium hydride), amides (such as lithium-diethylamide or lithium-diisopropylamide) or alcoholates, particularly alkali metal alcoholates, (such as potassium t-butylate or sodium methylate).

The process of reaction variant (a) according to the invention is preferably carried out in a temperature range from $-100°$ C. to $+20°$ C., in particular in a range between $-90°$ C. and $-40°$ C.

The reaction variant (a) usually takes place under normal pressure, but can also be carried out under increased pressure. The base used for the cyclisation is preferably employed in at least equivalent amounts. A 2- to 3-fold excess of base can be advantageous in some cases.

With knowledge of the start of the art, it could not have been expected that the compounds of the formula (II) would be cyclised under the given process conditions to give 4,4-disubstituted 1,4-dihydropyridines, especially since it was known from the state of the art that it is not possible to substitute the 4-position a second time by addition of organometallic compounds onto pyridine derivatives. It is thus to be described as exceptionally surprising that these new compounds which were hitherto inaccessible can be prepared by such a simple process.

Compounds of the present invention which are of particular interest are those in which (A) represents a phenyl, naphthyl, furyl, pyryl or pyridyl radical optionally containing 1, 2 or 3 identical or different substituents selected from phenyl, alkyl, alkenyl, alkinyl, alkoxy, alkylene, dioxyalkylene and alkylamino with in each case up to 4 carbon atoms, halogen, trifluoromethyl, trifluoromethoxy, nitro, cyano, azido and carboxamido, $R^3$ and $R^4$ are identical or different and each represent a hydrogen atom or an alkyl radical with up to 4 carbon atoms, a phenyl radical or a benzyl radical, $R^2$ and $R^5$ are identical or different and each represent a straight-chain, branched or cyclic, saturated or unsaturated hydrocarbon radical which has up to 8 carbon atoms, which is optionally interrupted in the chain by oxygen and is optionally substituted by halogen, pyridyl, phenyl or phenoxy, the phenyl or phenoxy radicals optionally being substituted by halogen, cyano, nitro or trifluoromethyl, $R^1$ represents a straight-chain, branched or cyclic, saturated or unsaturated aliphatic hydrocarbon radical which has up to 8 carbon atoms, which is optionally interrupted in the chain and is optionally substituted by phenyl, phenoxy, pyridyl or amino, the amino group optionally being substituted by two identical or different substituents selected from alkyl and alkoxyalkyl with in each case up to 4 carbon atoms, phenyl and benzyl, and the phenyl or phenoxy radical optionally being substituted by halogen, cyano, trifluoromethyl, nitro or alkyl, alkoxy or alkylamino with in each case 1 to 4 carbon atoms, and n is 0, 1 or 2.

Particularly preferred compounds of the present invention which may be mentioned are those in which (A) represents a phenyl, furyl, pyrryl or pyridyl radical optionally containing 1 or 2 identical or different substituents selected from phenyl, alkyl, alkoxy and alkylamino, with in each case 1 to 4 carbon atoms in the alkyl or alkoxy radicals, halogen, trifluoromethyl, trifluoromethoxy, nitro, cyano and azido, $R^3$ and $R^4$ are identical or different and each represent a hydrogen atom, an alkyl radical with 1 to 4 carbon atoms or a phenyl or benzyl radical, $R^2$ and $R^5$ are identical or different and each represent an alkyl radical which has 1 to 6 carbon atoms, and which is optionally interrupted in the chain by oxygen or is optionally substituted by halogen or phenyl, $R^1$ represents alkyl or alkinyl with up to 6 carbon atoms, the alkyl radical optionally being interrupted in the chain by one oxygen and optionally being substituted by phenyl, phenoxy or amino, and the amino group optionally being substituted by two identical or different substituents selected from alkyl with 1 to 4 carbon atoms, phenyl and benzyl, and n is 0 or 1.

The compounds of the present invention can be converted into sulphur-free products of the formula (III)

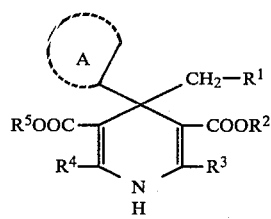

in a simple manner by known methods, for example by treatment with Raney nickel. (See Org. React. 12, 356–529 (1962) and Chem. Rev. 62, 374–404 (1962)). These 4,4-disubstituted 1,4-dihydropyridines of the formula (III) represent valuable pharmaceutically active compounds which can be used for the treatment of circulatory illnesses, preferrably as vasodilating, coronary, cerebral and blood pressure lowering agent (see U.S. Pat. Nos. 3,799,934 and 3,488,359).

The process according to the invention and the new compounds prepared in this way thus represent an advantageous route for the preparation of new pharmaceutically active substances.

The following Examples 1 to 6 relate to reaction variant (a) and Example 7 to 9 relate to reaction variant (b) and the Examples merely illustrate the process according to the invention.

EXAMPLE 1

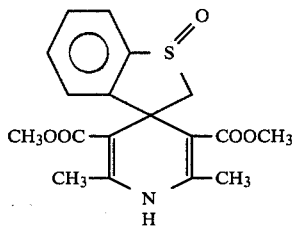

150 mmoles of 2,6-dimethyl-4-(2-methylsulphinylphenyl)-pyridine-3,5-dicarboxylic acid dimethyl ester were dissolved in 500 ml of anhydrous tetrahydrofuran, and 300 mmoles of lithium diisopropylamide were added at −78° C. Immediately thereafter, 50 ml of methanol, solid ammonium chloride and 1 liter of water were added. The precipitate was filtered off, washed in water and dried at 100° C. 4,3′-Spiro[2,6-dimethyl-3,5-bis-methoxycarbonyl-1,4-dihydropyridine]-[2′,3′-dihydro-1′-benzothiophene-1′-oxide] of melting point 286° to 289° C. (decomposition) was obtained. Yield: 80% of theory.

EXAMPLE 2

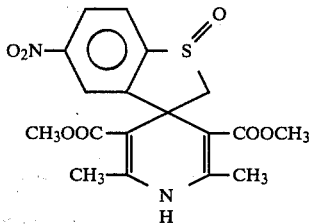

135 mmoles of 2,6-dimethyl-4-(2-methylsulphinyl-5-nitrophenyl)-pyridine-3,5-dicarboxylic acid dimethyl ester were dissolved in diethyl ether and reacted with 270 mmoles of potassium hydride at 20° C. and protonated. The solvent was evaporated off in a rotary evaporator, the residue was taken up in methylene chloride and the mixture was dried and evaporated again in a rotary evaporator. The residue crystallised on trituration with ethyl acetate.

4,3′-Spiro[2,6-dimethyl-3,5-bismethoxycarbonyl-1,4-dihydropyridine]-[5′-nitro-2′,3′-dihydro-1′-benzothiophene-1′-oxide] of melting point: 257°–259° C. (decomposition) was obtained.

Yield: 33% of theory.

EXAMPLE 3

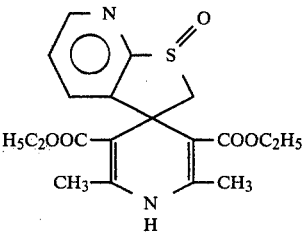

21 mmoles of 2,3-dimethyl-4-(2-methylsulphinylpyrid-3-yl)-pyridine-3,5-dicarboxylic acid diethyl ester were dissolved in dioxane, and the reaction with lithium diethylamide and working up were carried out analogously to Example 1.

4,3′-Spiro[2,6-dimethyl-3,5-bisethoxycarbonyl-1,4-dihydropyridine]-[2′,3′-dihydro-thieno-[2.3-b]pyridine-1′-oxide] of melting point 253°–256° C. was obtained. Yield: 27% of theory.

EXAMPLE 4

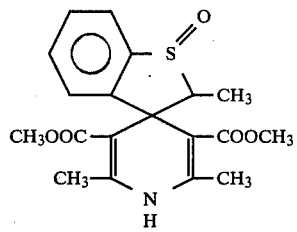

Analogously to Example 1, 125 mmoles of 2,6-dimethyl-4-(2-ethylsulphinylphenyl)-pyridine-3,5-dicarboxylic acid dimethyl ester were reacted with lithium diisopropylamide at −100° C. and protonated. The solvent was evaporated off in a rotary evaporator, the residue was extracted with methylene chloride and the mixture was dried over $Na_2SO_4$ and evaporated in a rotary evaporator. The residue was dissolved in acetone and the product was precipitated with ether. 4,4′-Spiro-[2,6-dimethyl-3,5-bismethoxycarbonyl-1,4-dihydropyridine]-[2′-methyl-2′,3′-dihydro-1′-benzothiophene-1′-oxide] was obtained as a diastereomer mixture with a melting point of 200°–206° C.

Yield: 41% of theory.

EXAMPLE 5

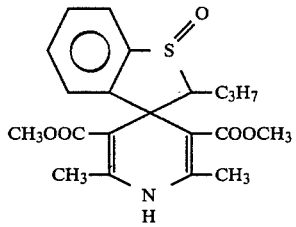

61 mmoles of 2,6-dimethyl-4-(2-propylsulphinylphenyl)-pyridine-3,5-dicarboxylic acid dimethyl ester were dissolved in toluene and reacted analogously to Example 1. 4,3′-Spiro[2,6-dimethyl-3,5-bismethoxy-carbonyl-1,4-dihydropyridine]-[2′-propyl-2′,3′-dihydro-1′- benzothiophene-1'-oxide] of melting point: 225°-229° C. remained.

Yield: 52% of theory.

EXAMPLE 6

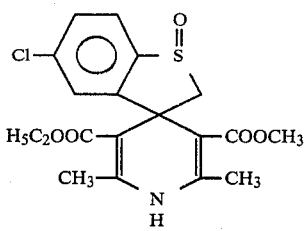

50 mmoles of 2,6-dimethyl-4-(2-methylsulphinyl-5-chloro-phenyl)-pyridine-3,5-dicarboxylic acid methyl ethyl ester were reacted analogously to Example 1. 4,3'-Spiro[2,6-dimethyl-3-methoxycarbonyl-5-ethoxycarbonyl-1,4-dihydropyridine]-[5'-chloro-2',3'-dihydro-1'-benzothiophene-1'-oxide] of melting point 210°-215° C. was obtained.

Yield: 44% of theory.

EXAMPLE 7

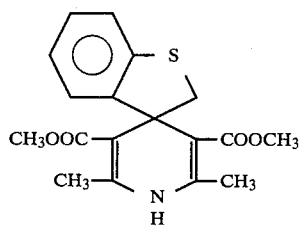

28 mmoles of 4,3'-spiro[2,6-dimethyl-3,5-bismethoxycarbonyl-1,4-dihydropyridine]-[2',3'-dihydro-1'-benzothiophene-1'-oxide] (obtained as described in Example 1) were dissolved in 500 ml of acetone and the solution was boiled under reflux with 100 g of Raney nickel (suspended in H$_2$O) for 45 minutes. After cooling, the mixture was filtered, the filtrate was evaporated in a rotary evaporator and the residue was recrystallised from diethyl ether. 4,3'-Spiro[2,6-dimethyl-3,5-bismethoxycarbonyl-1,4-dihydropyridine]-[2',3'-dihydro-1'-benzothiophene] with a melting point of 167°-168° C. was obtained.

Yield: 81% of theory.

EXAMPLE 8

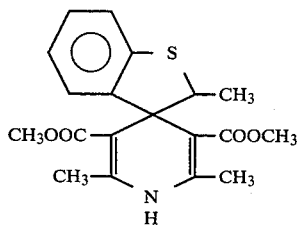

13 mmoles of 4,3'-spiro[2,6-dimethyl-3,5-bismethoxycarbonyl-1,4-dihydropyridine]-[2'-methyl-2',3'-dihydro-1'-benzothiophene-1'-oxide] (obtained as described in Example 4) in 150 ml of acetone were boiled under reflux together with 50 g of Raney nickel (suspended in H$_2$O) for 30 minutes, the mixture was filtered, the filtrate was concentrated and ether was added to the residue. 4,3'-Spiro[2,6-dimethyl-3,5-bismethoxycarbonyl-1,4-dihydropyridine]-[2'-methyl-2',3'-dihydro-1'-benzothiophene] with a melting point of 130°-131° C. was obtained.

Yield: 10% of theory.

EXAMPLE 9

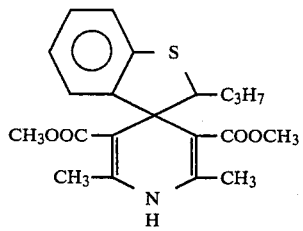

10 mmoles of 4,3'-spiro[2,6-dimethyl-3,5-bismethoxycarbonyl-1,4-dihydropyridine]-[2'-propyl-2',3'-dihydro-1'-benzothiophene-1'-oxide] (obtained as described in Example 5) in 200 ml of acetone were boiled under reflux together with 40 g of Raney nickel for 1.5 hours, the mixture was filtered, the filtrate was concentrated, the residue was chromatographed on silica gel using ethyl acetate (R$_F$=0.86) and the crystals were washed with a little ether. 4,3'-Spiro[2,6-dimethyl-3,5-bismethoxycarbonyl-1,4-dihydropyridine]-[2'-propyl-2',3'-dihydro-1'-benzothiophene] with a melting point of 160°-164° C. was obtained.

Yield: 41% of theory.

What is claimed is:

1. A compound of the formula

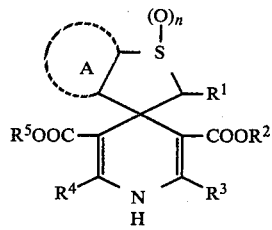

(I)

in which (A) represents a monocyclic or bicyclic carbocyclic aryl radical or a heterocyclic radical selected from furyl, pyrryl, pyrazolyl, imidazolyl, oxazolyl, isoxazolyl, pyridyl, pyridazinyl, pyrimidyl, pyrazinyl, quinolyl, isoquinolyl, indolyl, benzimidazolyl, quinazolyl or quinoxalyl, the said aryl radical or heterocyclic radical being unsubstituted or containing 1, 2 or 3 identical or different substituents selected from phenyl, C$_1$-C$_8$-alkyl, C$_1$-C$_8$-alkenyl, C$_1$-C$_8$-alkinyl, C$_1$-C$_8$-alkoxy, C$_1$-C$_6$-alkylene, C$_1$-C$_4$-dioxyalkylene, halogen, trifluoromethyl, trifluoromethoxy, C$_1$-C$_4$-alkylamino, nitro, cyano, azido and carboxamido, R$^3$ and R$^4$ are identical or different and each represent a hydrogen atom or an achiral straight-chain or branched C$_1$-C$_8$-alkyl radical, a monocyclic or bicyclic carbocyclic aryl radical or a monocyclic or bicyclic carbocyclic aryl-C$_1$-C$_4$-alkyl radical, said aryl and aralkyl radicals being unsubstituted or substituted by 1, 2 or 3 identical or different substituents selected from phenyl, C$_1$-C$_8$-alkyl, C$_1$-C$_8$- alkenyl, $C_1$-$C_8$-alkinyl, $C_1$-$C_8$-alkoxy, $C_1$-$C_6$-alkylene, $C_1$-$C_4$-dioxyalkylene, halogen, trifluoromethyl, trifluoromethoxy, $C_1$-$C_4$-alkylamino, nitro, cyano, azido and carboxamido on the aryl nucleus and containing 1 to 2 carbon atoms in the alkyl portion, $R^2$ and $R^5$ are identical or different and each represent a straight-chain or branched $C_1$-$C_8$-alkyl radical, which is optionally interrupted in the chain by oxygen and is optionally substituted by halogen, pyridyl, phenyl or phenoxy, the phenyl or phenoxy group optionally being substituted by halogen, cyano, di-$C_1$-$C_4$-alkylamino, $C_1$-$C_4$-alkoxy, $C_1$-$C_4$-alkyl, trifluoromethyl or nitro, $R^1$ represents a straight-chain or branched $C_1$-$C_8$-alkyl radical which is optionally interrupted in the chain by one oxygen and is optionally substituted by phenyl, phenoxy, pyridyl or amino, the phenyl, phenoxy or pyridyl radicals optionally being substituted by halogen, cyano, di-$C_1$-$C_4$-alkylamino, $C_1$-$C_4$-alkoxy, $C_1$-$C_4$-alkyl, trifluoromethyl or nitro, and the amino group optionally being substituted by two identical or different substituents selected from $C_1$-$C_4$-alkyl, $C_1$-$C_4$-alkoxy-$C_1$-$C_4$-alkyl, a monocyclic or bicyclic carbocyclic aryl and a monocyclic or bicyclic carbocyclic aryl-$C_1$-$C_4$-alkyl radical and n is 0, 1 or 2.

2. A compound according to claim 1, in which

A represents a phenyl, naphthyl, furyl, pyrryl or pyridyl radical optionally containing 1, 2 or 3 identical or different substituents selected from phenyl, alkyl, alkenyl, alkinyl, alkoxy, alkylene, dioxyalkylene and alkylamino with in each case up to 4 carbon atoms, in each alkyl, alkenyl, alkinyl or alkoxy group, $C_1$-$C_6$-alkylene, $C_1$-$C_4$-dioxyalkylene, halogen, trifluoromethyl, trifluoromethoxy, nitro, cyano, azido and carboxamido, $R^3$ and $R^4$ are identical or different and each represent a hydrogen atom or an alkyl radical with up to 4 carbon atoms, a phenyl radical or a benzyl radical, $R^2$ and $R^5$ are identical or different and each represent a straight-chain or branched $C_1$-$C_8$-alkyl radical, which is optionally interrupted in the chain by oxygen and is optionally substituted by halogen, pyridyl, phenyl or phenoxy, the phenyl or phenoxy group optionally being substituted by halogen, cyano, di-$C_1$-$C_4$-alkylamino, $C_1$-$C_4$-alkoxy, $C_1$-$C_4$-alkyl, trifluoromethyl or nitro, $R^1$ represents a straight-chain or branched $C_1$-$C_8$-alkyl radical which is optionally interrupted in the chain by one oxygen and is optionally substituted by phenyl, phenoxy, pyridyl or amino, the phenyl, phenoxy or pyridyl radicals optionally being substituted by halogen, cyano, di-$C_1$-$C_4$-alkylamino, $C_1$-$C_4$-alkoxy, $C_1$-$C_4$-alkyl, trifluoromethyl or nitro, and the amino group optionally being substituted by two identical or different substituents selected from $C_1$-$C_4$-alkyl, $C_1$-$C_4$-alkoxy-$C_1$-$C_4$-alkyl, a monocyclic or bicyclic carbocyclic aryl and a monocyclic or bicyclic carbocyclic aryl-$C_1$-$C_4$-alkyl radical and n is 0, 1 2.

3. A compound according to claim 1, in which (A) represents a phenyl, furyl, pyrryl or pyridyl radical optionally containing 1 or 2 identical or different substituents selected from phenyl, alkyl, alkoxy and alkyl-amino, with in each case 1 to 4 carbon atoms in the alkyl or alkoxy radicals, halogen, trifluoromethyl, trifluoromethoxy, nitro, cyano and azido, $R^3$ and $R^4$ are identical or different and each represent a hydrogen atom, an alkyl radical with 1 to 4 carbon atoms or a phenyl or benzyl radical, $R^2$ and $R^5$ are identical or different and each represent an alkyl radical which has 1 to 6 carbon atoms, and which is optionally interrupted in the chain by oxygen or is optionally substituted by halogen or phenyl, $R^1$ represents alkyl or alkinyl with up to 6 carbon atoms, the alkyl radical optionally being interrupted in the chain by one oxygen and optionally being substituted by phenyl, phenoxy or amino, and the amino group optionally being substituted by two identical or different substituents selected from alkyl with 1 to 4 carbon atoms, phenyl and benzyl, and n is 0 or 1.

4. A compound according to claim 1 which is 4,3'-Spiro[2,6-dimethyl-3,5-bis-methoxycarbonyl-1,4-dihydropyridine]-[2'3'-dihydro-1'-benzothiophene-1'-oxide].

5. A compound according to claim 1 which is 4,3'-Spiro[2,6-dimethyl-3,5-bismethoxycarbonyl-1,4-dihydropyridine]-5'-nitro-[2',3'-dihydro-1'-benzothiophene-1'-oxide].

6. A compound according to claim 1 which is 4,3'-Spiro[2,6-dimethyl-3,5-bisethoxycarbonyl-1,4-dihydropyridine]-[2',3'-dihydro-thieno-[2.3-b]-pyridine-1'-oxide].

7. A compound according to claim 1 which is 4,4'-Spiro-[2,6-dimethyl-3,5-bismethoxycarbonyl-1,4-dihydropyridine]-2'-methyl-[2',3'-dihydro-1'-benzothiophene-1'-oxide].

8. A compound according to claim 1 which is 4,3'-Spiro[2,6-dimethyl-3,5-bismethoxy-carbonyl-1,4-dihydropyridine]-[2',3'-hydro-1'-benzothio-phene].

9. A process for the production of a compound according to claim 1, which comprises cyclizing (a) a pyridine of the formula

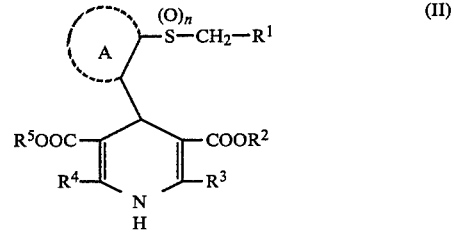

in which $R^1$, $R^2$, $R^3$, $R^4$, $R^5$, n and A have same meanings as in claim 1, at a temperature between $-120°$ C. and $+30°$ C. in the presence of a base to give a spiro compound of claim 1, and (b) if a compound of claim 1 in which n is 0 is desired and the product of reaction variant (a) is a sulphinyl compound, reducing said sulphinyl compound by means of Raney nickel.

10. A process according to claim 9, in which reaction variant (a) is carried out in the presence of an inert organic solvent.

11. A process according to claim 9, in which reaction variant (a) is carried out in a temperature range from $-90°$ to $-40°$ C.

12. A process according to claim 9, 10 or 11 in which the cyclization is carried out in the presence of a 2- to 3-fold excess of base.

* * * * *